(12) United States Patent
Levin et al.

(10) Patent No.: US 7,054,480 B2
(45) Date of Patent: May 30, 2006

(54) SYSTEM AND METHOD FOR PROCESS VARIATION MONITOR

(75) Inventors: Evgeni Levin, Rehovot (IL); Gilad Almogy, Givatayim (IL); Efrat Rozenman, Asseret (IL)

(73) Assignee: Applied Materials Israel, Ltd., Rehovot (IL)

( * ) Notice: Subject to any disclaimer, the term of this patent is extended or adjusted under 35 U.S.C. 154(b) by 0 days.

(21) Appl. No.: 11/038,449

(22) Filed: Jan. 18, 2005

(65) Prior Publication Data

US 2005/0122510 A1 Jun. 9, 2005

Related U.S. Application Data

(63) Continuation of application No. 10/155,255, filed on May 22, 2002, now Pat. No. 6,862,491.

(51) Int. Cl.
*G06F 19/00* (2006.01)
*G01N 21/88* (2006.01)
*G06K 9/00* (2006.01)

(52) U.S. Cl. ............... 382/154; 356/237.1; 356/237.5; 250/559.27; 358/106

(58) Field of Classification Search .. 356/237.1–237.6, 356/630, 72–73; 250/559.27, 559.19, 559.22, 250/559.4; 438/14–16; 382/139, 154; 358/106, 358/101
See application file for complete search history.

(56) References Cited

U.S. PATENT DOCUMENTS

| 4,845,558 | A | | 7/1989 | Tsai et al. |
|---|---|---|---|---|
| 5,293,538 | A | | 3/1994 | Iwata et al. |
| 5,450,201 | A | * | 9/1995 | Katzir et al. ................. 356/369 |
| 5,563,702 | A | * | 10/1996 | Emery et al. ................. 356/73 |
| 5,594,235 | A | | 1/1997 | Lee |
| 5,909,276 | A | | 6/1999 | Kinney et al. |
| 5,991,699 | A | | 11/1999 | Kulkarni et al. |
| 6,122,046 | A | | 9/2000 | Almogy |
| 6,137,570 | A | * | 10/2000 | Chuang et al. .......... 356/237.5 |
| 6,407,373 | B1 | * | 6/2002 | Dotan ..................... 250/201.3 |
| 6,456,899 | B1 | | 9/2002 | Gleason et al. |
| 6,484,306 | B1 | | 11/2002 | Bokor et al. |
| 6,489,624 | B1 | * | 12/2002 | Ushio et al. ........... 250/559.27 |
| 6,570,650 | B1 | * | 5/2003 | Guan et al. .............. 356/237.4 |
| 6,673,637 | B1 | * | 1/2004 | Wack et al. .................. 438/14 |
| 2002/0165636 | A1 | | 11/2002 | Hasan |
| 2003/0063791 | A1 | | 4/2003 | Smilansky et al. |

OTHER PUBLICATIONS

Applied Materials, Inc., PCT/US2003/016569, International Search Report, Oct. 30, 2003, 5pp.

* cited by examiner

*Primary Examiner*—Gregory J. Toatley, Jr.
*Assistant Examiner*—Sang H. Nguyen
(74) *Attorney, Agent, or Firm*—Tarek N. Fahmi

(57) ABSTRACT

A method to extend the process monitoring capabilities of a semiconductor wafer optical inspection system so as to be able to detect low-resolution effects of process variations over the surface of a wafer at much higher sensitivity than heretofore possible. The method consists, in essence, of grouping sensed pixels by geometric blocks over the inspected surface and comparing each block with a corresponding one from another die on the same wager, from another wager of from a stored model image. In one embodiment of the invention, pixel values are compared directly and differences are thresholded at a considerably lower level than during a defects detection process. In another embodiment, there is calculated a signature for each block, based on the sensed light intensity values, and corresponding signatures are compared.

2 Claims, 3 Drawing Sheets

SYSTEM AND METHOD FOR PROCESS VARIATION MONITOR

RELATED APPLICATIONS

This application is a Continuation of U.S. patent application Ser. No. 10/155,255, filed May 22, 2002 now U.S. Pat. No. 6,862,491, incorporated herein by reference.

FIELD OF THE INVENTION

This invention relates to the field of semiconductor wafer inspection and, in particular, to a system and method for optically monitoring variations in the integrated-circuit fabrication process.

BACKGROUND OF THE INVENTION

The process of fabricating integrated circuits (ICs) on a semiconducting substrate, such as a silicon wafer, is highly complex and consists of a large number of steps. Each step involves many process parameters that must be tightly controlled in order to obtain consistent and accurate results. There are, however, physical factors that may cause unintentional deviations in the process at any step.

Such factors may be due to variations in the substrate itself, to slight mechanical and optical inaccuracies in the processing equipment (such as defocusing due to slight misalignment), to dust and dirt and to environmental variations. The deviations in the process may be a function of time that is between successive wafers, or between various parts of any one wafer, or both. When any of these process deviations becomes excessive, singly or in combination, defects may appear in some features of the IC. These defects may be manifested in one of two scales: (a) as deviations of the surface appearance, observable over a considerable area and therefore with low resolution, which are usually due to slight geometric deviations (such as in the width of conductors), and (b) as more noticeable geometric distortions in minute areas, observable at full optical resolution. We shall refer to the former (those on scale "a") as "macro-defects" and to the latter (those on scale "b") as "micro-defects", sometimes also as just "defects".

Since the geometry of modern ICs is defined in units on the order of 0.1–0.2 microns, the slight deviations observable in macro-defects, while occurring over large areas, must be measured with resolutions down to the order of tens of nanometers or better, which can be done only at shorter than optical wavelengths.

Micro-defects, on the other hand, are generally (and by definition) of sizes such as to be detectable through optical microscopy. They may be due to microscopic disturbances in the process, such as dust particles, or they may be, as they often are, extreme manifestations of macro-defects.

Commonly, wafers in process are inspected periodically, e.g., after certain processing steps, in order to detect defects and to thus monitor the process.

Currently, the entire top surface of the wafer is inspected only optically and that—with special apparatus that is designed to detect micro-defects. An example of such apparatus is the Compass inspection system, sold by Applied Materials of Santa Clara, Calif.; its essential parts, notably the optical system, illustrated by the block diagram in FIG. 1, include a light beam source, such as a laser source, optics for collimating, focusing and scanning the light beam, a wafer holder, for holding and moving the inspected wafer, at least one sensor and a processor for processing the signals from each sensor.

Detected defects are analyzed as to their number and, preferably, as to their nature. Obviously, the occurrence of a relatively large number of defects within any region, or over the entire wafer, attests to some fault or unacceptable deviation in the process and should alert the operator to try to identify the physical factor causing the deviation and to take proper remedial action, e.g., appropriately adjusting process parameters. In the case of a very large number of defects, a determination is possibly made to reject certain dies or possibly the entire wafer.

Often, detected defects are closely examined and analyzed at a separate, so-called review, phase of operation, in order to learn therefrom about the nature of the responsible process deviation or about the existence of a macro-defect and its nature, from which, again, the responsible process deviation may be deduced. Such examination is generally done at a higher resolution than that used for defects detection and may involve micro metrology techniques. It may be carried out by means of the same equipment, but often is done on a separate, very high resolution, device, such as a scanning electron microscopes (SEW-which is extremely expensive.

This current-art procedure of learning about process deviations that cause macro-defects in the fabricated ICs by detecting micro-defects, and possibly reviewing them, has two major drawbacks: Firstly and most importantly, macro-defects must be fairly severe in order for detectable resultant micro-defects to appear; there is then a risk of deleterious further deviation in the process before it is remedied; in extreme cases, the detected defects, whether micro or macro, may already be excessive, requiring wafer rejection-which obviously represents economical loss. Secondly, the close examination and analysis of defects during the review phase involves time and costly equipment; the time delay may cause additional wafers to be adversely affected before the process deviations have been identified and corrected. It is noted that the first drawback could be averted if the entire surface could be inspected at high resolution; this procedure is, however, extremely slow and, as mentioned above, requires very expensive equipment.

There is thus a clear need for a method and apparatus that would inspect the entire surface of wafers in process, directly detecting macro-defects at levels that do not necessarily result in micro-defects and thereby providing early, or more sensitive, indications of process variations. There is, moreover, a need for such process variation monitoring apparatus to be relatively inexpensive and therefore to preferably share some parts with conventional optical defects detecting apparatus.

SUMMARY OF THE INVENTION

The invention is, in essence, of a method to extend the process monitoring capabilities of a semiconductor wafer optical inspection system so as to be able to detect, and possibly quantify, macro-defects, i. e. low-resolution effects of process variations over the surface of a wafer, at much higher sensitivity than possible by analyzing micro-defects conventionally detected in such a system; optionally it enables also detecting effects of temporal process variations on successively processed wafers. The method is preferably operative simultaneously, and in conjunction, with micro-defects detection operation of such an optical inspection system and, in common with it, involves examining the entire inspectable surface of the wafer. The method of the invention is designed to detect process variations of lower magnitude than such that would result in a significant number of detectable micro-defects. It is noted that the simultaneity feature and the feature of entire surface examination, mentioned above, advantageously contrast with the mode of operation of process monitoring methods of current art, whereby geometric effects of process variations are examined only at those areas in which micro-defects have been detected and, moreover, such examination is carried out at a so-called review phase, which is separate from the defects detection operation and during which a higher-resolution scan is required-possibly even using different equipment.

In one embodiment of the invented system, partial results of the defects detection operation are further processed to directly obtain indications of process variations over the entire inspected area. Also in common with the defects detection operation, the invented method can advantageously use the outputs of any multiple sensors comprised in the inspection system, such as those disposed along various angles to the inspected surface and to the illuminating beam, including sensing a so-called dark field or a so-called bright field, to sense more varied effects and thus obtain more accurate or more reliable results. The invented method can also form a basis for a capability of classifying process variations whose effects have been detected and measured by it, although the embodiments to be described below do not include such a capability.

Optionally and with obvious modifications, the invented method can function separately from, or independently of, defects detection operation, although, it is noted, combined operation is generally more economical. The invention is also of equipment and system operative to carry out the method as disclosed herein.

It will be appreciated that, though the present disclosure describes the invention in terms of inspecting semiconductor wafers, being processed to become integrated-circuit dies, the invention is equally applicable to the inspection of surfaces of other substrates, such as those carrying photonic devices or those undergoing any other processing, as well as surface variations not necessarily ascribable to a process. It will be appreciated that the invention is equally applicable to the inspection of surfaces by means other than optical, such as an electron-or ion beam, and, in general, to any inspection system whereby the surface is probed or sensed point-by-point. In any such system each sensor outputs intensity values that correspond to energy received by the sensor as a result of reflection of the probing beam from the inspected surface. These values are generally called radiation intensity values, but in the sequel will also be referred to, interchangeably, as light intensity values (since the preferred embodiments utilize a light beam for the probing).

The invented method, as applicable to a wafers inspection system, basically comprises the following logical steps: (a) Obtaining one or more light intensity values for each point (pixel) on the inspected surface, belonging to corresponding classes, such as the outputs of the various sensors in the inspection system; these may be identical to the values used for micro-defects detection; (b) preferably calculating for each pixel one or more derived values; (c) dividing the surface into an array of geometric blocks, each block including a considerable plurality of contiguous pixels; (d) calculating for each block, as a whole, a so-called signature, which is a set or an array of variables, as a function of the light intensity values and the derived values of its several pixels; (e) for each block, comparing its signature with a designated comparison signature, possibly associated with a comparison block, and thereby calculating one or more process deviation indications.

The derived values in step b are preferably local spread values, i.e., a measure of the extent of variability of intensity values in the immediate vicinity of the referenced pixel; they are calculated separately with respect to each class (i.e., sensor).

In one embodiment of the method, calculating a signature includes calculating for each pixel, and, a with respect to each class, a histogram over pairs of light intensity-and spread values. In one configuration, there is provided for each block over the surface of the wafer a model comparison signature and the comparing in step e is with respect to that model signature. In another configuration, the comparison with respect to any block, is between any signature calculated for the currently inspected wafer and a corresponding one calculated for the previously inspected one. In yet another configuration, applicable to the prevalent case that the IC being fabricated is an array of identical dies, the array of blocks is defined in alignment with the array of dies, there being a plurality of blocks over each die; the comparing of signatures is between any block and a congruent block over one or more other dies.

In another embodiment of the invented method, applicable particularly when also micro-defects are being detected, there are first obtained for each pixel, and corresponding to each sensor, a light intensity value and possibly a local spread value-both in comparison with corresponding ones for a congruent pixel on another die. The differences yielded by such comparisons are preferably thresholded according to a given threshold curve and each excess is noted; the threshold values of the given curve are typically much lower than those applied in a similar procedure during detection of defects. Finally, the excesses, corresponding to each sensor, are counted over each block, the sums forming the respective process deviation indications.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

The method of the invention is preferably embodied as an additional computer program, runable on a digital processor resident in a wafer inspection system, which normally serves to detect defects after certain wafer processing stages. A particular example of such an inspection system, which will be used herein to illustrate the method, is the Compass inspection system, sold by Applied Materials of Santa Clara Calif., mentioned in the Background section above and shown schematically in FIG. 1. It should however be understood that the method of the invention can also be embodied, with obvious modifications, as an appropriate program on any processor in other inspection systems, including those that serve to inspect surfaces other than semiconductor wafers. It should likewise be understood that the method of the invention can also be embodied, with obvious modifications, in a system specifically or solely designed for it, for the purpose of process variation monitoring only.

Figure 1:
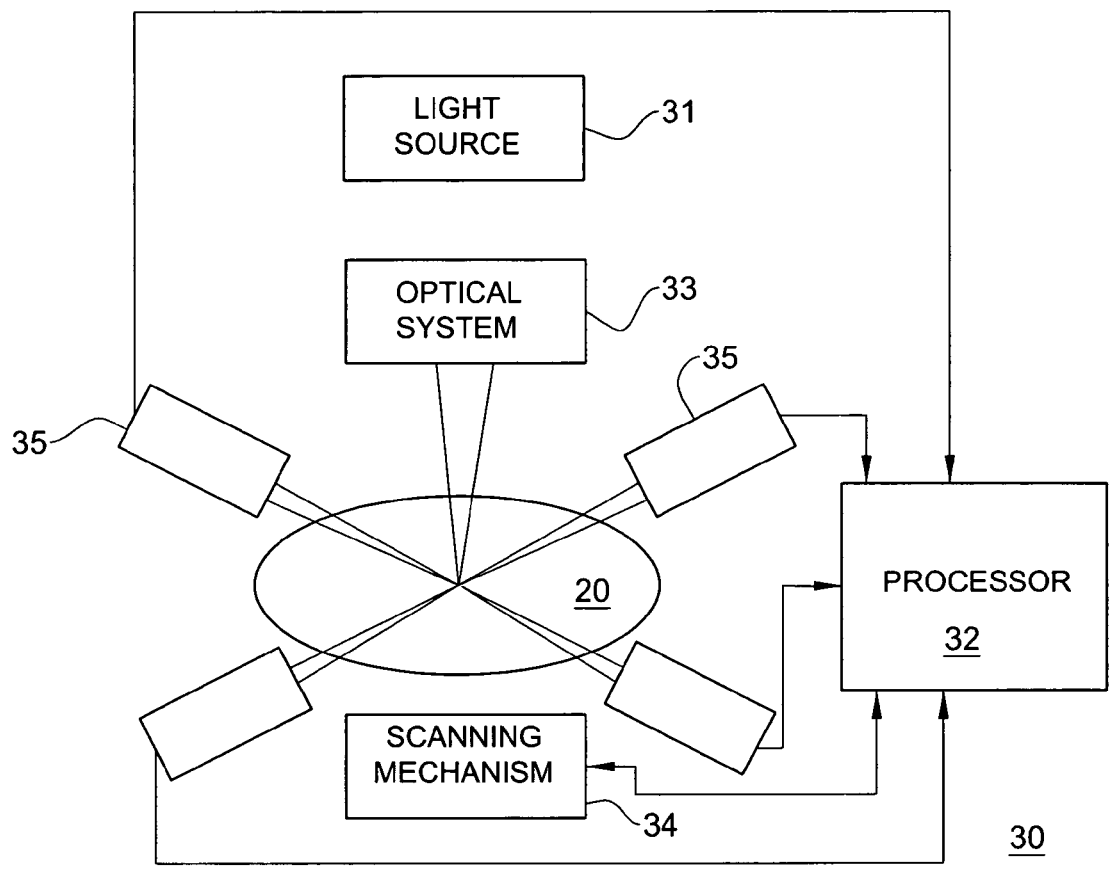
FIG. 1 is a schematic diagram of a wafer inspection system used in an embodiment of the invention.

In the inspection system 30 of FIG. 1, a light source 31, preferably a laser, and an optical system 33 project a focused light spot normally onto the surface of a wafer 36. The wafer is moved by a scanning mechanism 34 so as to be scanned by the focused spot in a regular raster of parallel lines. Light reflected or scattered from the surface into various directions is collected by sensors 35 and is converted to corresponding electrical signals; these are sampled at regular intervals and digitized, to produce corresponding light intensity values-to be hence referred to as intensities. The intensities are fed to processor 32, which is usually programmed to perform analysis of the signals so as to determine defects, but preferably is also programmed to perform the analysis according to the method disclosed herein. The position of the beam on the surface that corresponds to any one sampling is known as a respective pixel. The distance between the scan lines determines the distance between adjacent pixels along one axis and the ratio between the sampling rate and the scanning speed determines the distance between adjacent pixels along the orthogonal axis. Typically, this distance, along each axis is between 0.5 and 2 micrometers. Preferably one sensor collects light reflected normally and is referred to as bright-field sensor, four sensors collect light reflected at a large angle to the normal (at corresponding four azimuth directions) and are referred to as dark-field sensors, and one ring-shaped sensor collects light reflected at a small-to-medium angle to the normal and is referred to as gray-field sensor. The same descriptors apply also to the corresponding digital intensity values; more generally, however, the intensities from the various sensors may be regarded as belonging to corresponding different classes and will be referred to as such in the sequel.

Different classes of light intensities may also be associated with other parameters affecting the scanning and the sensing of reflected light, such as spectral differences.

Figure 2:
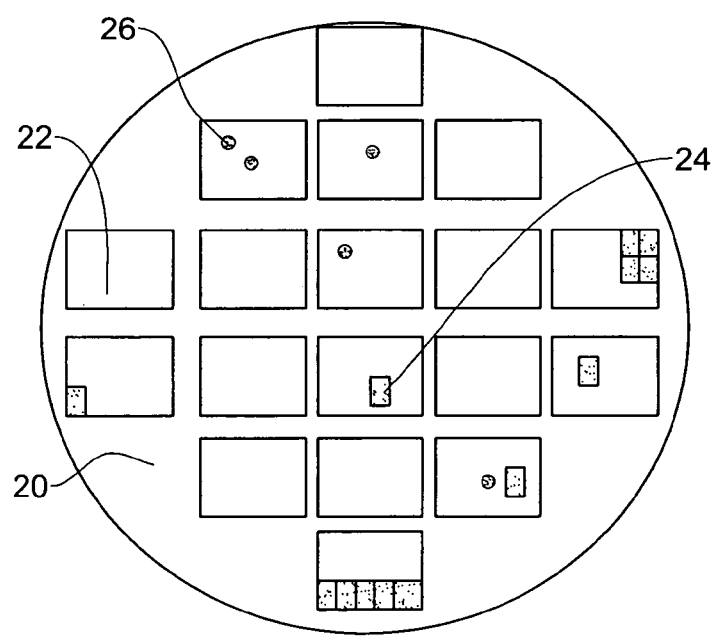
FIG. 2 is a schematic diagram of the surface of a wafer, showing the relationship between pixels, blocks and dies according to the invention.

In most fabrication situations, a semiconductor wafer is processed to produce a regular array of identical circuit patterns, to become dies (also known as chips), as illustrated in FIG. 2, which schematically shows die areas 22 in relation to a wafer 20. Accordingly, defects 26 are usually detected by comparing values obtained from each die 22 with those obtained from one or more other dies 22 on the wafer or, alternatively, from a model ("golden") die.

More specifically, the following procedure is typically carried out for each pixel and for each class of intensity values (of the six classes associated with the six sensors): The intensities of the pixel and of a group of neighboring pixels (e.g. the immediately adjacent pixels) are mutually compared, to yield corresponding spread values S. A particular comparison function is, for example, finding the highest-and the lowest intensity values and calculating the absolute difference between them.

The six intensity values I and the six corresponding spread values S are compared with those of a pixel at an identical position with respect to another die. Preferably the other die is the one just previously scanned by the laser beam, but it may be another one on the wafer, or a model die. The resultant array of 24 numbers (I and S values from each of the two dies for each of the six classes) is analyzed, applying suitable algorithms and parameters, to determine whether the pixel is defective. In general, such algorithms and parameters includes classifying the circuit pattern in which the pixel is located, on the basis of known combinations of ranges of the I and S values, and defining deviation thresholds, i. e. maximum acceptable deviations, for the various values for each class of pattern. When the difference between the two dies, with respect to one or several sensed values, exceeds the pertinent deviation threshold, the pixel is suspect of being defective. A pixel that is thus suspect, on the basis of comparison with two other dies, or with a model die, is determined to be defective. It is again noted that the number of sensors and corresponding intensity values per pixel need not be six, as in this exemplary system, but may be any number, including one.

According to an embodiment of the present invention, the array of pixels over the surface of the wafer is logically divided into contiguous rectangular blocks, each containing an array of, typically, 500×100 pixels. The blocks, in turn, form a Cartesian array. Preferably the array of blocks is aligned with the array of dies, so that all dies are identically divided into blocks. The relation between them is shown in FIG. 2, where each die 22 is seen to be identically divided into a number of blocks 24 (only few of which are shown in the drawing). If the pixels are spaced 2 micrometers, the size of a block 24 would typically be 1×1 millimeter and a typical die, of gross size 10 millimeter, would contain 10×10 blocks.

Figure 3:
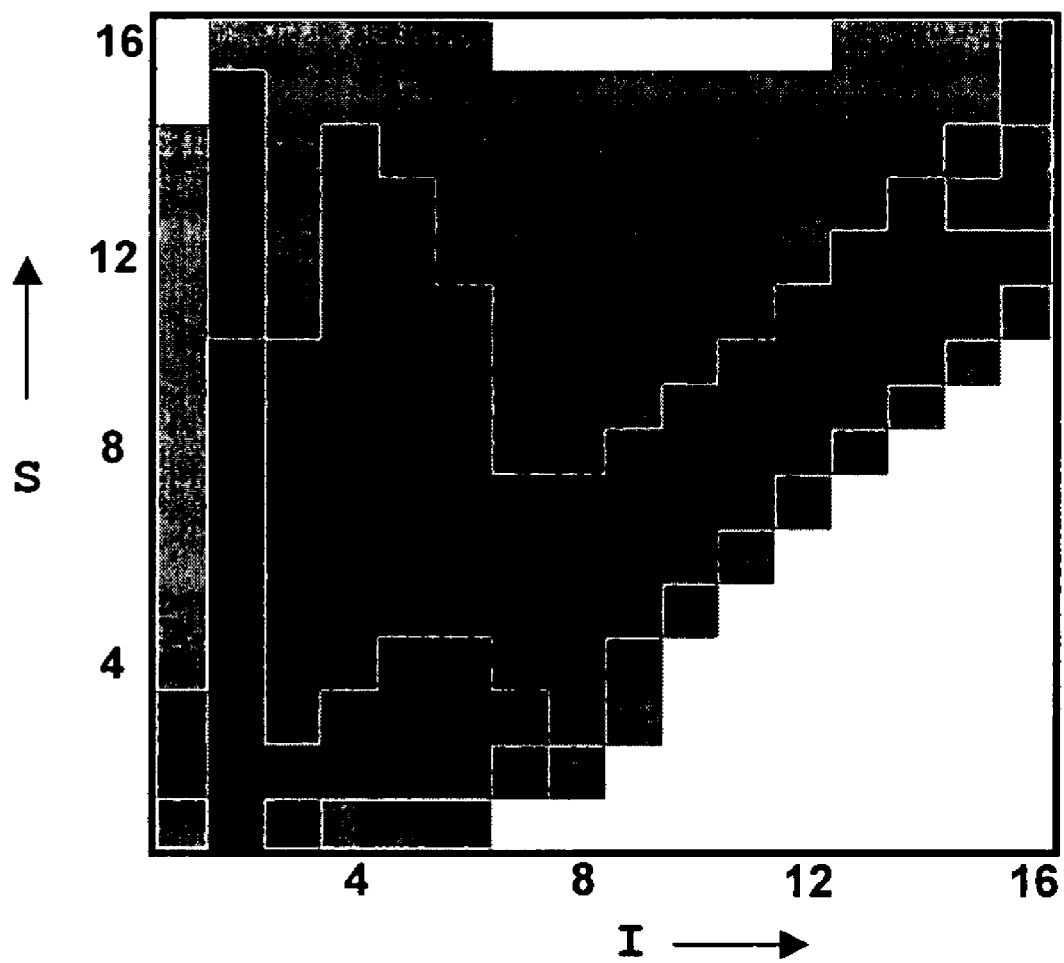
FIG. 3 is a diagram showing a typical block histogram, used in an embodiment of the invention.

Now, for each block and for each class (i.e., sensor) there is preferably computed a histogram of the number of pixels sharing any pair of values I and S. The histogram, to be referred to as Block Characteristic Histogram (BCH), may be visualized as a two-dimensional array, one axis representing 256 values of I and the other 256 values of S (assuming that each value is represented by an 8-bits number). It is noted that a typical distribution of values in a BCH depends on the type of the circuitry underlying the particular block, as well as on the class of I values. For example, in the BCH that corresponds to a Dark-Field sensor there will typically be a predominance of medium intensity values and medium spread values for a memory circuit region, characterized by a uniform pattern, while for a bare silicon (sparse circuitry) both intensity and spread values are predominantly low. A typical histogram for a bright-field sensor and a memory region is shown schematically in FIG. 3, where, for the sake of clarity and simplicity, the number of values of I and of S are only 16 each. It would be appreciated that the two variables underlying the histogram need not be I and S, but may be any other values derived from the light intensities.

The set of BCHs (six in this exemplary preferred embodiment) is a particular type of a so-called signature of the block. Other types of signatures are possible within the present invention and are calculable for each block, either from its BCHs or directly from its intensities and any derived variables (such as the spread values). One simple example of such a signature is a set of any of the averages of the values (e.g., I or S or both) for each class over the block. As another example of signature calculation, all the intensities for which the respective spread value is under a certain threshold (signifying sparse circuit region) are averaged.

An example of a function computable for each class, either directly or from a respective BCH, to produce a block signature, is the correlation between spread and intensity values. Other types of block signatures may include, for example, functions of the plurality of BCHs related to the block.

There will thus be created a signature for each block over the surface of the wafer. It is noted that, with some types of signatures, the parameters governing their calculation may vary from block to block-to suit various types of underlying patterns (i. e. various types of circuitry). Next, for each block at a time, to be referred to as a current block, its signature, to be referred to as a current signature, is compared with a so-called comparison signature, to yield a set of one or more so-called process variation indications for the block. Any such comparison is preferably governed by one or more parameters-usually defining ranges of allowable deviations; these are determined, again, preferably as a function of the underlying circuitry patterns. The collection of all such comparison parameters, as well as the above-mentioned parameters governing the formation of signatures, over the area of the wafer or of any one die, form together a parameters map of the wafer or the die; such a map is determined once for each type of die whose processing is being monitored.

Several configurations of the preferred embodiment of the invention, differentiated by the source of the comparison signature, are contemplated.

According to a first configuration, serving for absolute process variation detection, there is preliminarily defined a model signatures map-over the entire surface of the wafer, or over the area of a single die (assuming a pattern of identical dies over the wafer). Such a map is preferably produced for each type of a die (i.e., circuit pattern) or each batch of production and may be generated, for example, by subjecting one or more samples known to be perfect to the above-described scanning and signature computation process. During inspection, the signature for each block is compared with the corresponding one in the model map. According to a second configuration of this embodiment, serving for inter-wafer process variation detection, the signature for each block is compared, during inspection, with the corresponding one in a previously inspected wafer, preferably the immediately preceding one. A third configuration, serving for die process variation detection and applicable to the case of a pattern of identical dies over the wafer, is similar to the second configuration, except that during inspection, the signature for each block is compared with that of a corresponding block in one or more other dies, preferably-adjacent dies. This configuration may be applied more generally for any surface on which there are repetitive identical instances of any given pattern on the surface being inspected.

As discussed above, each comparison process is governed by comparison parameters taken from the parameters map (which generally vary among the blocks). A typical example of a comparison process, applicable to the case that a signature is a single number, possibly one per class, is simply computing the absolute difference between the corresponding numbers in the current signature and the comparison signature and determining whether any computed difference exceeds a corresponding threshold in the parameters map; if it does, a suitable process variation indication is assigned to the current block.

Another example of a comparison process, applicable to the case that a signature is a BCH of I and S values, is as follows: For each class, an average absolute difference value is computed, by absolutely subtracting, for each pair of I and S values, corresponding entries in the current BCH and the comparison BCH from each other and averaging the results. The maximum average difference from among all classes is then compared with a corresponding threshold in the parameters map, to possibly yield an indicative process variation value. According to a modification of the latter exemplary method there is defined in the parameters map, for each class and each block, a set of deviation thresholds as a function of I and S values; the differences between entries in the current BCH and the comparison BCH are compared with corresponding deviation thresholds and any excess yields a deviation flag; the existence of a deviation flag from any of the class-related BCHs associated with the block, and possibly the number of such flags, is indicative of the occurrence of any process variation, possibly-of its magnitude.

It is noted that the pixel light intensity values, used by the method, and possibly also the spread values, are essentially the same used for defects detection, if the system also serves for that. Sharing of the system, in this way, by the defects detection process and by the process variation monitoring of the present invention is thus extremely economical. Moreover, the two procedures may be simultaneous, thus saving time. Nevertheless, the method of the invention may also be implemented in a stand-alone system, essentially as described hereabove.

Another embodiment of the invention, which is particularly adapted to serve cooperatively with a defects detection system, is as follows: The intensities sensed at each pixel and, possibly, the derived spreads are compared with those of a corresponding pixel on another die, to be referred to as a comparison die, in a manner similar to that employed in defects detection. However, the threshold of deviation is in this case set at considerably lower levels than for defects detection.

Figure 4:
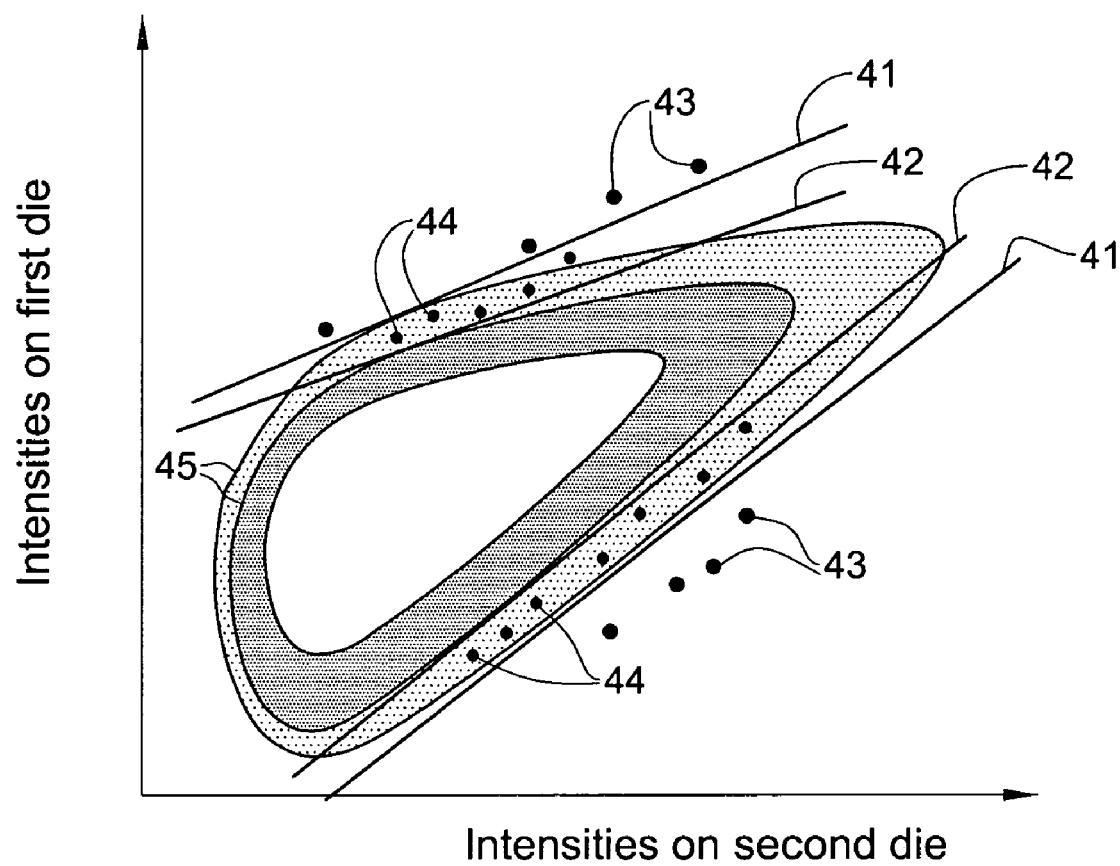
FIG. 4 is a diagram showing a typical normal distribution of pixel values and typical threshold curves used for defects detection, according to prior art, and for process deviation measurement according to a second configuration of the invention.

Thus generally, a much larger number of pixels will have intensity and spread values that unacceptably deviate from the comparison values. These are marked as abnormal pixels. As in the first preferred embodiment, the area of the wafer, and of each die, is logically divided into blocks. The number of abnormal pixels in each block is counted and blocks with high count are reported as exhibiting a process deviation. Again, the procedure is carried out with respect to each class (e.g., sensor). The process may be illustrated by a comparison histogram, a simplified example of which (typical for a certain circuit region) is shown schematically in FIG. 4, where the two axes represent values of intensity in the first and second die, respectively. For each combination of intensity values, the number of pixels within a block, for which that combination occurs, is recorded. Ideally, all entries would be along a certain section of the main diagonal, but, owing to process"noise" and variations, there actually are many pixels with unequal values in the two dies. In FIG. 4 there are drawn typical contour lines 45 that delineate distribution levels of value pairs, the innermost contour, for example, including 90 percent of all pixels sensed. Two pairs of threshold lines, approximately parallel to the main diagonal, are drawn at some chosen relation to the contours 45; in effect, they divide the histogram area into five regions. A first pair of lines 41, farther from the diagonal, serves to distinguish defective pixels 43, while a second pair of lines 42, closer to the diagonal, serves to distinguish abnormal pixels 44. It is noted that lines 41 are those used in a prior art inspection system, such as the aforementioned Compass system, to distinguish defects and may optionally be used also in the system of the invention; however, lines 42 and their use to distinguish abnormal pixels are a novel feature of the invention. In any case, all pixels with values outside lines 42 (including those possibly outside lines 41) are preferably counted as abnormal.

It is possible to devise also formulas that consider the counts of abnormal pixels corresponding to various sensors differentially, or in a weighted sum manner, and to thus gain additional information about the process variation being monitored; all these will be generally referred to as calculating a relationship between the pixel abnormality indications. In another configuration of this embodiment, the comparison values are taken from a model die and may be stored; more generally, the comparison values may be regarded as forming a suitable comparison array of values (which is derived either from the comparison die or from the model die).

When applying any of the methods of the invention within a process variation monitoring system (which may be part of a wafer inspection system), deviations, which are reported block-by-block as described above, may be presented graphically to the fabrication process operator, for him to deduce the process variation that may have caused them. Alternatively, the reported data may be automatically applied to an interpretation process, which will output information about the possible process variations or the data may be otherwise processed.

Another alternative is to initiate review type inspection (e.g., high resolution observation) with respect to reported blocks, possibly certain blocks with particularly high deviation scores. It is noted that these reviewable locations will, in general, be additional to those indicated by defects (detected by current methods), though some of the locations may be approximately identical. It is further noted that the manner of applying results of the method to process monitoring, as discussed for example in the present paragraph, are outside the scope of the invention and are mentioned by way of illustrating its utility.

It would be appreciated that many variations of the methods described hereabove, including various other configurations and functions, as well as applications to other types of surfaces, patterns and processes, are possible-all coming within the scope of the invention, which is solely defined by the following claims.

It will also be understood that the system according to the invention may be a suitably programmed computer or digital processor. Likewise, the invention contemplates a computer program being readable by a computer for executing the method of the invention. The invention further contemplates a machine-readable memory tangibly embodying a program of instructions executable by a machine for executing the method of the invention.

What is claimed is:

1. A method for bright field inspection, comprising: bright field illuminating a wafer to receive multiple images of multiple dies; measuring light intensity values for select pixels and groups of neighboring pixels thereof associated with each of the multiple dies; and performing a die-to-die comparison based upon the measured light intensity values.

2. A bright field inspection system, comprising: a device for scanning a wafer and obtaining multiple bright field images of multiple dies; and a processor configured for measuring light intensity values for select pixels and groups of neighboring pixels thereof associated with the each of multiple dies, and performing a die-to-die comparison based upon the measured light intensity values.

* * * * *